United States Patent
Maier et al.

(10) Patent No.: US 8,894,621 B2
(45) Date of Patent: *Nov. 25, 2014

(54) SELF-DESTRUCTING TRANSDERMAL THERAPEUTIC SYSTEM HAVING IMPROVED FUNCTIONALITY AND EFFICACY

(71) Applicant: LTS Lohmann Therapie-Systeme AG, Andernach (DE)

(72) Inventors: Stefan Maier, Leverkusen (DE); Margit Wirz, Polch (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/851,575

(22) Filed: Mar. 27, 2013

(65) Prior Publication Data
US 2013/0226108 A1    Aug. 29, 2013

Related U.S. Application Data

(63) Continuation of application No. 12/935,085, filed as application No. PCT/EP2009/002205 on Mar. 26, 2009, now Pat. No. 8,435,219.

(30) Foreign Application Priority Data

Apr. 2, 2008 (DE) .................. 10 2008 016 804

(51) Int. Cl.
*A61M 35/00* (2006.01)
(Continued)

(52) U.S. Cl.
CPC ............... *A61K 9/703* (2013.01); *B09B 3/0075* (2013.01); *A62D 3/00* (2013.01); *A61K 9/7084* (2013.01); *B09B 2220/14* (2013.01); *A61K 9/7061* (2013.01); *A61K 31/485* (2013.01); *A61K 9/7092* (2013.01)
USPC .......................... 604/290; 424/10.2; 424/449

(58) Field of Classification Search
CPC ... A61K 9/703; A61K 9/7084; A61K 9/7092; A61K 31/485; A62D 3/00
USPC .................................. 604/290; 424/10.2, 449
See application file for complete search history.

(56) References Cited

U.S. PATENT DOCUMENTS

| 4,917,676 | A | 4/1990 | Heiber et al. |
| 7,838,715 | B2 | 11/2010 | Uhland et al. |

(Continued)

FOREIGN PATENT DOCUMENTS

| WO | WO 90/04965 A1 | 5/1990 |
| WO | WO 02/085268 A1 | 10/2002 |

(Continued)

OTHER PUBLICATIONS

Transdermale Pflaster; Spektrum der Wissenschaft Oct. 2003, 42-43.

(Continued)

*Primary Examiner* — Tatyana Zalukaeva
*Assistant Examiner* — Andrew J Mensh
(74) *Attorney, Agent, or Firm* — ProPat, L.L.C.

(57) ABSTRACT

The invention relates to a self-destructing transdermal therapeutic system (TTS), preferably in the form of a transdermal patch, that includes an active ingredient, an agent rendering the active ingredient useless, and a perforation mechanism. The perforation mechanism allows a mobile phase to reach the agent that is capable of rendering the active ingredient useless after removing the TTS after use. The agent then comes into contact with the active ingredient and destroys the active ingredient in the presence of the mobile phase.

11 Claims, 2 Drawing Sheets

(51) Int. Cl.
  *B09B 3/00* (2006.01)
  *A61K 9/44* (2006.01)
  *A61K 9/70* (2006.01)
  *A62D 3/00* (2006.01)
  *A61K 31/485* (2006.01)

(56) References Cited

U.S. PATENT DOCUMENTS

| | | | | |
|---|---|---|---|---|
| 8,075,912 | B2 * | 12/2011 | Hoffmann et al. | 424/449 |
| 2004/0241218 | A1 | 12/2004 | Tavares et al. | |
| 2005/0163717 | A1 | 7/2005 | Anderson et al. | |
| 2007/0166233 | A1 | 7/2007 | Royds | |

FOREIGN PATENT DOCUMENTS

| | | | |
|---|---|---|---|
| WO | WO 2004/037259 | A1 | 5/2004 |
| WO | WO 2004/098576 | A1 | 11/2004 |
| WO | WO 2005/041883 | | 5/2005 |
| WO | WO 2007/137732 | A2 | 12/2007 |

OTHER PUBLICATIONS

Polymers in Transdermal Drug Delivery Systems, S. Kandavilli et al., Pharmaceutical Technology, May 2002, 62-80.

* cited by examiner

SELF-DESTRUCTING TRANSDERMAL THERAPEUTIC SYSTEM HAVING IMPROVED FUNCTIONALITY AND EFFICACY

CROSS-REFERENCE TO RELATED APPLICATIONS

This continuation application claims priority to allowed parent application, U.S. patent application Ser. No. 12/935,085 filed Sep. 28, 2010, which claims priority to PCT/EP 2009/002205 filed Mar. 26, 2009 and German Patent Application No. 10 2008 016 804.1, filed Apr. 2, 2008. Each of U.S. patent application Ser. No. 12/935,085; International Application PCT/EP 2009/002205 and German Patent Application 10 2008 016 804.1 are hereby incorporated by reference herein in their entirety.

FIELD OF THE INVENTION

The invention relates to a transdermal therapeutic system (TTS), or else called transdermal patch, which possesses the inherent property of self-destructing after use. The TTS of the invention comprises an active therapeutic ingredient, preferably from the group of analgesics, which is brought up to the skin from the system by diffusion and is then administered transdermally for therapeutic purposes.

BACKGROUND OF THE INVENTION

Transdermal administrations of the active ingredients buprenorphine and fentanyl are the drug forms of choice for the treatment of chronic pain in long-term therapy. The continuous delivery of such highly active analgesics via the skin provides a continuous supply of a constant dose of analgesic to a patient with pain, thereby preventing plasma peaks and plasma troughs. This has the advantage that, by virtue of a low but sufficient plasma concentration of the active ingredient, there is occurrence neither of side effects due to overdose nor of avoidable states of pain due to undersupply. The skilled worker is aware, for example, of the commercial products TRANSTEC®, but also DUROGESIC® or DUROGESIC SMAT®, which have proven useful in the therapy of pain for some considerable time.

The disadvantage of the TTS in the therapy of pain, however, is that in order to maintain the so-called concentration gradient and hence the therapeutically desired plasma level of the active ingredient throughout the period of administration of the TTS it is always necessary for the store quantity of active ingredient present in the TTS to be greater than that actually delivered to the patient. A consequence of this is that worn TTS constitute a potential for abuse by, for example, those involved in the drugs scene. These groups of persons are perfectly capable of collecting worn TTS and extracting them with the most primitive of means in order to obtain the residual active ingredient still present and to consume it abusively in order to appease their drug addiction.

In the past, therefore, there has been no lack of attempts to prevent this unregulated misuse by advising patients to shred worn patches and then put them down the toilet into the sewerage system. A disadvantage of this method is that neither legislators nor drug manufacturers are able to guarantee that this recommendation is also reliably followed by the patients; moreover, mass disposal through the sewerage system constitutes an environmental problem which should not be underestimated.

Consequently, TTS were developed which as well as the active ingredient also contained an antagonist (e.g., WO 2004/098576 whose United States equivalent is U.S. Pat. No. 7,182,955; WO 90/04965 and WO 2004/037259 whose United States equivalent is United States Publication No. 2005/214223). The intention was to prevent, or at least significantly hinder, the above-described obtaining or abusive extraction of the active analgesic ingredient from used TTS. These protective measures, however, proved not to be enough to prevent medicament abuse, since it continues to be the case that the active ingredient itself can be separated from the antagonist by relatively simple means, by fractional precipitation.

WO 2007/137732 describes a TTS which in addition to an active ingredient further comprises an agent which is separate from the active ingredient, and which makes the active ingredient useless, in a solution. Additionally present to this end is a means which, following use of the TTS, allows the agent, therefore, to enter into contact with the active ingredient and make it useless. The disadvantage of this otherwise ideal solution, however, is that the agent in solution, on account of its high reactivity, restricts the shelf life, and that, in some cases, the risk exists of damage by liquid leakage in the course of transit as well.

SUMMARY OF ADVANTAGEOUS EMBODIMENTS OF THE INVENTION

It was an object of the present invention, therefore, to provide a TTS with which, following proper use, an abusive removal of the remaining active ingredient remains almost completely impossible and which, additionally, can be stored without problems over a relatively long time period, and, furthermore, is not subject to in-transit damage through unintended leakage of agent dissolved in liquid.

This object is achieved through the provision of a TTS, preferably in the form of a transdermal patch to be applied to the surface of the patient's skin, which following use, i.e., after removal of the TTS from the surface of the patient's skin, destroys itself. Self-destructing TTS means, in accordance with the application, that the residual active drug ingredient present in the TTS, after use, is directly or indirectly destroyed, chemically decomposed and/or made useless. At the same time, however, it is always ensured that this destruction process is not commenced even before or still during the transdermal administration of the TTS.

DETAILED DESCRIPTION OF ADVANTAGEOUS EMBODIMENTS OF THE INVENTION

Figure 1A:
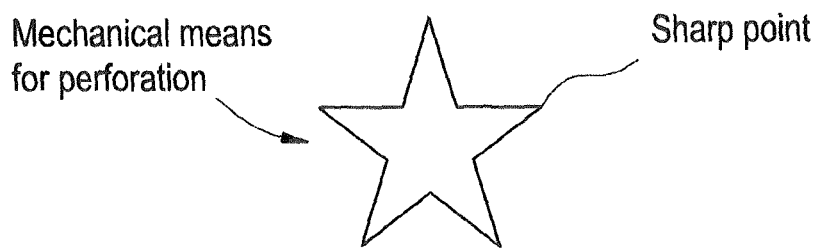
FIG. 1A is a top view illustration of an exemplary TTS geometry exhibiting a sharp-pointed contour.

The invention accordingly provides a transdermal therapeutic system (TTS) of the generic type specified above, preferably in the form of a transdermal patch, which comprises at least one active therapeutic agent and a substance or substance mixture (agent) which is spatially separate from said active ingredient and which is able, preferably by chemical reaction, to destroy, decompose or in any case make useless the active ingredient, said TTS comprising at least one additional mechanical means for perforation, which undoes the separation of active ingredient from agent on removal of the TTS from the patient's skin, by allowing a mobile phase to enter.

The effect of the mobile phase is that the agent is activated and in activated form is brought into contact with the active ingredient, which as a result of this contact is decomposed, destroyed and so made useless in terms of its activity.

The agent may be a substance or a substance mixture which may be present in accordance with the invention as a solid or as a paste. The agent is preferably a substance which reacts chemically with the active ingredient and thereby destroys it, more particularly a chemical oxidizing agent such as, for example, inorganic reagents, such as permanganates, e.g., potassium permanganate, manganese dioxide, lead dioxide, lead tetraacetate, cerium(IV) salts, chromates, osmium tetroxide, nitrites, such as potassium nitrite, selenium dioxide, peroxo compounds, hypohalides, or sulfur; preferably potassium permanganate and potassium nitrite. Organic oxidants, such as dimethyl sulfoxide, N-bromosuccinimide, quinones, hypervalent iodine compounds, peracids and peresters, but also enzymes, may be employed. The agent for a given active ingredient is preferably selected on the basis of its chemical reactivity with the active ingredient.

The active ingredient is preferably an active ingredient from the group of analgesics such as, for example, narcotics. Mention should preferably be made of morphine derivatives, heroin and buprenorphine, or fentanyl and its derivatives sufentanil and alfentanyl. In principle, all other combinations of active ingredient and agent can be used for which transdermal administration via a TTS is a suitable administration form.

Separation between the active ingredient and the agent is normally accomplished by a layer which is permeable to liquids but impermeable to solids, such as a paper, membrane or nonwoven fabric, for example. The nonwoven fabric here may be comprised of mineral fibers, such as glass, mineral wool or basalt, animal fibers such as silk or wool, plant fibers such as cotton, or chemical fibers made from natural polymers (e.g., cellulose) and/or synthetic polymers, for example. Synthetic plastics employed for this purpose may be standard polymers such as, for example, polyamide, polyimide, polytetrafluoroethylene, polyethylene, polypropylene, polyvinyl chloride, polyacrylates or polymethacrylates, polystyrene, polyesters or polycarbonates.

On removal of the patch/TTS from the patient's skin, the separation between active ingredient and agent is undone such that ingress of liquid to the agent takes place or at least becomes possible. The liquid approaches the agent, dissolves it, activates it in so doing, and so helps the agent to move through—for example, the nonwoven fabric, come into direct contact with the active ingredient, and destroy it in the process.

The means which accomplishes or enables the ingress of liquid is a mechanical means, which may occur in different forms. The intention thereby is that it should in any case be ensured that, on any removal of the TTS, independently of the direction of peeling, the means fulfils its intended function, namely that of allowing, directly or indirectly, the undoing of the separation between active ingredient and agent, an event which, however, must not occur at any earlier time. For this purpose, the means possesses a multiplicity of sharp or pointed regions. The simplest embodiment of such a means is a star.

A star is shown by way of example in FIG. 1A. Such a star may have sharp points, spikes or edges, which, when the flexural radius or the mechanical stress on the TTS reaches a certain point, lead to perforation of at least one adjacent layer, which may be, for example, a wall of a liquid store or a separating film, and which thus accomplish or at least allow the ingress of liquid.

In one preferred embodiment the mechanical means for perforation possesses a blunt outer contour and a sharp or pointed internal region.

Figure 1B:
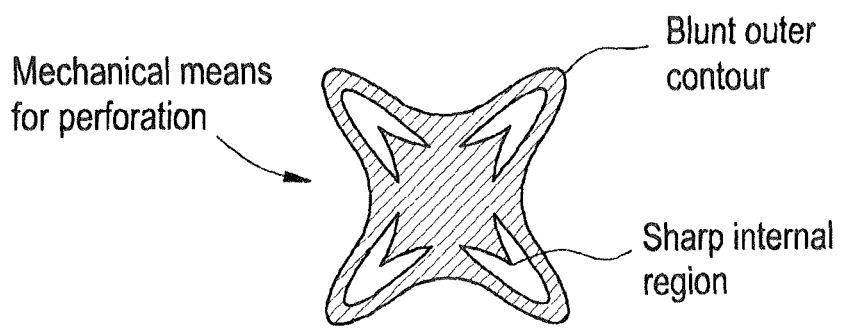
FIG. 1B is a top view illustration of an exemplary TTS geometry exhibiting a blunt outer contour and a pointed internal region.
Figure 1C:
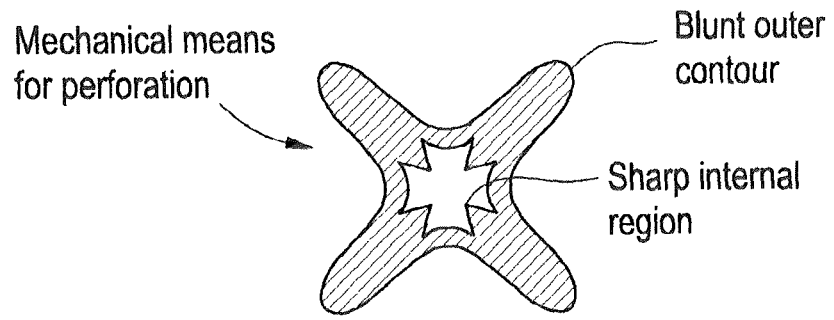
FIG. 1C is a top view illustration of an alternative exemplary TTS geometry exhibiting a blunt outer contour and a pointed internal region.

Examples of an inventively preferred geometry of this kind are shown in FIG. 1B and FIG. 1C. Both representations show geometries with a round, blunt and hence de-sharpened outer margin, which in accordance with the invention are used preferably. With this geometry, indeed, there is no longer a risk of perforation taking place prematurely and unintendedly in the course of production, storage or transit, or during proper handling, and hence of the active ingredient being destroyed even before it is used. The pointed, sharp regions lie protected in the interior of the geometry. At large flexural radii and/or under low force on the TTS, therefore, perforation is not initiated. Only on removal of the TTS from the skin is the flexural radius sufficiently small, or the mechanical forces acting sufficiently large, in order, through distortive bending of the structure, to rotate the corresponding point in the inner region, around pivots dictated by the geometry, by an angle of up to a maximum of 90°, out of the plane in the direction of the adjacent layer. The tension in the system that is achieved as a result of the stiffness of the material produces perforation of at least one adjacent layer.

It is particularly useful for the mechanical means that perforates at least one adjacent layer to possess a size which is adapted to the areal extent of the TTS, and preferably it is only slightly smaller than the internal area of the TTS. This on the one hand ensures a sufficient flexibility of the system, while on the other hand the tension in the structure that is achieved by bending is sufficient to perforate the adjacent layer. In addition, apart is also played by the ratio of the length of the point to the total length of the means in force direction. The shorter the length of the point, the more sensitive the system, since shortening the point length increases its stiffness in relation to the total length of the means. As a result of the action of force such as tension upwardly on removal of the TTS, the point is swiveled about its pivot point/points and then pressed at an acute angle in the range from 20 to 90 through at least one adjacent layer.

A suitable material for the mechanical means is, for example, a flexible plastic of sufficient stiffness. Plastics having such properties are, for example, standard polymers such as polyethylene or polypropylene, polyesters such as polyethylene terephthalate, and also other polymers such as cycloolefin copolymers, polyacrylates or polymethacrylates, polytetrafluoroethylene, PVC, polycarbonate, polystyrene, perfluoroalkoxy, perfluorethylenepropylene, etc. The thickness of material influences the efficacy in proper service. The plastics are used in thicknesses of 100 to 1000 µm, preferably of 200 to 700 µm, more preferably of 250 to 550 µm. As a result of the preferred geometry of the means, namely the ratio of the length of the point to the overall length, and as a result of the arrangement of the pivot points, the TTS is highly flexible and feels pleasant to wear, in spite of the stiffness of the material, without loss of the self-destruction functionality.

Figure 2:
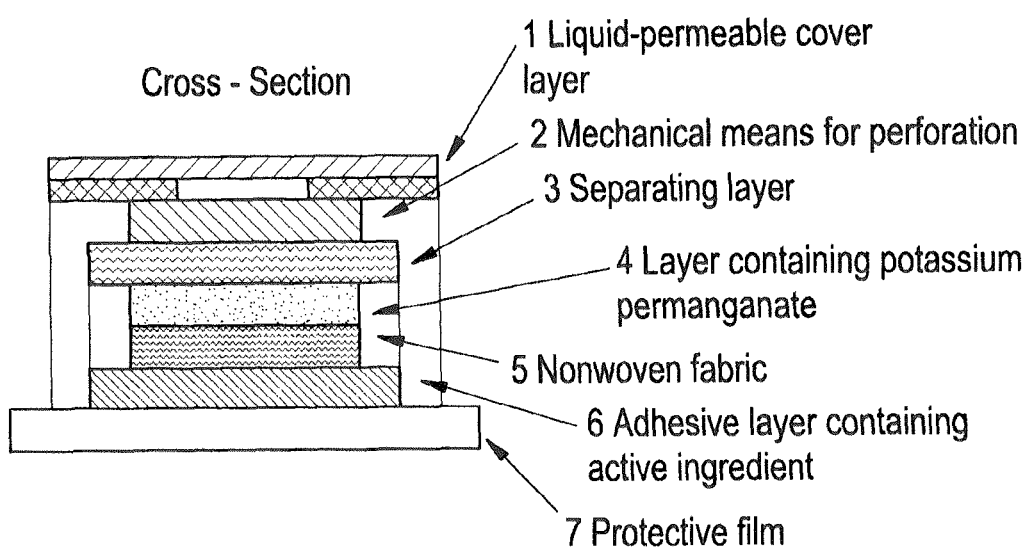
FIG. 2 is a cross-sectional illustration of a TTS of the invention with an exemplary multilayer construction.

The TTS of the invention possesses in principle a multilayer construction, for which one possible variant will be elucidated by way of example in the exemplary embodiment attached as FIG. 2.

FIG. 2 shows a vertical section through a TTS of the invention with one possible multilayer construction. This construction comprises, in the representation, at least one top cover layer 1 which is permeable, for example, to liquids and is made, for example, from woven fabric colored in skin color, which on its bottom face is coated, at least in regions, with a thin layer of adhesive, and a bottom adhesive layer 6, which on proper use of the TTS is in direct skin contact and in which the active ingredient is incorporated. From this layer, the active ingredient is delivered to the uppermost layer of the skin, the epidermis.

Also possible is a membrane patch design, in which an adhesive membrane is disposed between an active ingredient reservoir and the skin, and delivers the active ingredient to the epidermis and is capable of controlling the rate of delivery.

Between the top cover layer 1, which is designed, for example, to be regionally permeable to liquids, and a separating layer 3 which in its initial state is impermeable, for example, to liquids, there is located at least the mechanical means for perforation 2. Located beneath the separating layer 3 is a reservoir 4 for the agent for destroying the active ingredient, preferably an oxidizing agent in solid form; below that there is a nonwoven fabric 5, and below that the layer 6 of adhesive, already mentioned above, with the active ingredient. Provided for storage and transportation of the TTS, additionally, below the layer 6 of adhesive, is a transparent protective film 7, which is to be removed before the TTS is used.

In another preferred embodiment of the invention, there may be a sealed pouch with a store of liquid arranged beneath the top cover layer 1, and the mechanical means for perforation may also be situated in said pouch.

The TTS or transdermal patch of the invention may otherwise be produced using all of the materials that are known for such systems to the skilled worker.

For producing the TTS of the invention, therefore, the skilled worker may in principle employ the materials, production methods, and construction of the TTS or transdermal patches known from the prior art, having additionally—in accordance with the invention—a suitable combination of means and agent (in this regard cf.: Transdermale Pflaster; Spektrum der Wissenschaft October 2003, 42; Transdermal Controlled Systemic Medications, Y. W. Chien, Drugs and the Pharmaceutical Sciences, Vol. 31; Polymers in Transdermal Drug Delivery Systems, S. Kandavilli et al., Pharmaceutical Technology, May 2002, 62-80).

A precondition for the suitability of plastics for medical applications of this kind, besides favorable physical properties such as mechanical strength, low inherent weight, and adequate processing properties, is primarily an effective sterilizability, for hygiene reasons. These requirements are adequately met by, for example, polyethylene, polypropylene, polyvinyl chloride, polystyrene, polymethacrylates, polyamides, polyesters, and polycarbonates.

The invention is elucidated in more detail by the examples below, without being restricted thereto. It is nevertheless possible for specific configurations of the TTS of the invention, as described in the examples, to be generalized as such, individually or in combination with one another, as preferred features for the invention.

Example 1

Added to 1.14 kg of a solution of a self-crosslinking polyacrylate, consisting of the monomers 2-ethylhexyl acrylate, vinyl acetate, butyl acrylate, and acrylic acid, in a mixture of the organic solvents ethyl acetate, heptane, and isopropanol/toluene, were 100 g of levulinic acid, 150 g of oleyl oleate, 100 g of polyvinylpyrrolidone, 150 g of ethanol, 200 g of ethyl acetate, and 100 g of buprenorphine base. This mixture was stirred over a period of about 2 hours until homogeneous. Following homogenization, the mixture was applied to the siliconized face of a 100 μm polyester film, after which the solvents were removed by drying in a drying cabinet at 70° C. for 10 minutes. The coated thickness in the coating was selected such that removal of the solvents produced a weight per unit area of approximately 80 g/m$^2$. Following removal of the solvents, the laminate comprised of siliconized polyester film and polymer layer containing active ingredient was lined with a second, less strongly siliconized polyester film. Thereafter the resultant laminate was cut into squares with an edge length of 5×5 cm. The 5×5 cm siliconized polyester film was then removed on one side of the laminate, and an absorbent, liquid-permeable material, a nonwoven fabric for example with a size of 4×4 cm, for example, was adhered centrally. A filter paper pouch with embossed margins, filled with potassium permanganate in powder form, was then placed onto the absorbent, liquid-permeable nonwoven fabric, the design of the pouch being such that its overall area was smaller than that of the polymer layer containing active ingredient.

Without restricting the invention, the pouch may have dimensions of 4×4 cm. The potassium permanganate-filled pouch then had a separating layer, impermeable to liquids and measuring 5×5 cm, applied atop it, and bonded at the margins to the polymer layer containing active substances. Applied subsequently was a four-point Maltese cross, in the manner shown in FIG. 1C, made from hard polymer material. In a subsequent operation, a liquid-permeable top cover film, in the form of a laminate comprised of a regionally applied, active ingredient-free, pressure-sensitive adhesive layer and woven fabric colored in skin color, of thickness 21 μm, was adhered in such a way that the active ingredient-free layer of pressure-sensitive adhesive projects all round at the margin beyond the polymer layer containing active ingredient. Finally, the remaining second siliconized polyester film with a size of 5×5 cm was removed form the polymer layer containing active ingredient and was replaced by a protective film having the same dimensions as those of the top cover film.

When the TTS is applied in the context of its proper, intended use, it is necessary first of all to remove the siliconized polyester layer (protective film) which is easy to accomplish. When the TTS is adhered to a patient's skin, the liquid-impermeable separating layer remains intact to start with. Liquid is unable to access the potassium permanganate powder. When, however, after the administration time of 1 to 7 days, the TTS is removed from the patient's skin, at least one point of the four-point Maltese cross pierces the separating layer, owing to the stiffness of the polymer material, and automatically perforates said layer. The Maltese cross geometry ensures that the separating layer is perforated in any case, irrespective of the direction in which the TTS is removed from the patient.

If the used TTS is then placed in water, the water is able to penetrate the TTS through the cover film and the perforation in the separating layer, to dissolve the potassium permanganate, and to transport it to the remaining active ingredient in the bottom layer of adhesive within a short time, through the absorbent nonwoven fabric. In said bottom layer of adhesive, an oxidation process is immediately initiated, and in the case of, for example, buprenorphine results in its oxidative destruction. Placing the used TTS in water ensures that the active ingredient cannot be misused.

Example 2

Example 1 was repeated, with the difference that, between the top cover layer and the pouch with the potassium permanganate in powder form, a liquid-tight pouch with all-round sealing, filled with the Maltese cross and a quantity of 1.5 ml of water, was bonded in. On removal of the used TTS from the patient's skin, at least one point of the Maltese cross pierces the lower wall of the liquid pouch and thus brings about the egress of the water, which enters immediately into contact with the potassium permanganate disposed below it.

In this embodiment of the invention, the patient need not place the used TTS in water in order to initiate the destruction procedure; instead, the TTS self-destructs automatically on removal after use.

That which is claimed:

1. A method of self-destroying a transdermal therapeutic system comprising
providing a transdermal therapeutic system comprising at least one active ingredient, at least one agent which makes the active ingredient useless, at least one separation layer permeable to liquids but impermeable to solids between the active ingredient and the agent which makes the active ingredient useless, and at least one mechanical means for perforation adjacent a liquid impermeable layer, said mechanical means for perforation possessing a blunt outer contour and a sharp or pointed internal region,
applying the transdermal therapeutic system to a patient's skin;
removing the transdermal therapeutic system from the patient's skin and thereby perforating the liquid impermeable layer with the sharp or pointed internal region of the mechanical means for perforation, said perforating step ensuring that a mobile phase can approach the agent which makes the active ingredient useless, and
contacting the active ingredient and the agent which makes the active ingredient useless with one another, thereby destroying the active ingredient by this contact.

2. The method of self-destroying a transdermal therapeutic system as claimed in claim 1, wherein the method further comprises activating the agent which snakes the active ingredient useless via the mobile phase.

3. The method of self-destroying a transdermal therapeutic system as claimed in claim 1, wherein the method further comprises chemically reacting the active ingredient and the agent which makes the active ingredient useless in the presence of the mobile phase.

4. The method of self-destroying a transdermal therapeutic system as claimed in claim 3, wherein the agent which makes the active ingredient useless is an oxidizing agent.

5. The method of self-destroying a transdermal therapeutic system as claimed in claim 1, wherein, said perforating step comprises distortive bending of said mechanical means for perforation during removal, thereby rotating at least one point in the internal region around pivots dictated by its geometry, by an angle of up to a maximum 90° out of a plane in a direction of an adjacent layer.

6. The method of self-destroying a transdermal therapeutic system as claimed in claim 5, wherein said rotating step comprises rotating step comprises swiveling the point by an angle in the range from 20 to 90° through at least one adjacent layer.

7. The method of self-destroying a therapeutic system as claimed in claim 1, wherein said liquid impermeable layer is a wall of a sealed pouch containing a liquid store and said method further comprises situating the mechanical means for perforation in said sealed pouch.

8. The method of self-destroying a therapeutic system as claimed in claim 1, wherein said method further comprises filling a filter paper pouch with agent which makes the active ingredient useless in powder form.

9. A self-destructing transdermal therapeutic system comprising at least one active ingredient, at least one agent which makes the active ingredient useless, at least one separation between the active ingredient and the agent which makes the active ingredient useless, and at least one mechanical means for perforation, wherein said mechanical means for perforation possesses a blunt outer contour and a sharp or pointed internal region, said sharp or pointed internal region perforating the separation between the active ingredient and the agent which makes the active ingredient useless upon removal of the TTS after use, said perforation ensuring that a mobile phase can approach the agent which makes the active ingredient useless, thereby allowing the active ingredient and the agent which makes the active ingredient useless to come into contact with one another and destroy the active ingredient by this contact.

10. The self-destructing transdermal therapeutic system as claimed in claim 9, wherein said sharp or pointed internal region has either (i) a Maltese cross-shape or (ii) a square-with-elongated corners-shape.

11. The self-destructing transdermal therapeutic system as claimed in claim 9, wherein said mechanical means for perforation is formed from plastic ranging in thickness from 100 to 1000 microns.

* * * * *